(12) United States Patent
Drontle et al.

(10) Patent No.: US 10,363,402 B2
(45) Date of Patent: Jul. 30, 2019

(54) SINUS DILATION CATHETER

(71) Applicant: ENTELLUS MEDICAL, INC., Plymouth, MN (US)

(72) Inventors: John R. Drontle, Monticello, MN (US); Anthony J. Hanson, Chaska, MN (US)

(73) Assignee: Entellus Medical, Inc., Plymouth, MN (US)

( * ) Notice: Subject to any disclaimer, the term of this patent is extended or adjusted under 35 U.S.C. 154(b) by 0 days.

(21) Appl. No.: 15/345,322

(22) Filed: Nov. 7, 2016

(65) Prior Publication Data

US 2017/0113027 A1 Apr. 27, 2017

Related U.S. Application Data

(63) Continuation of application No. 15/139,052, filed on Apr. 26, 2016, which is a continuation of application (Continued)

(51) Int. Cl.
*A61B 17/24* (2006.01)
*A61M 29/02* (2006.01)
(Continued)

(52) U.S. Cl.
CPC .............. *A61M 29/02* (2013.01); *A61B 17/24* (2013.01); *A61B 34/20* (2016.02); *A61B 34/30* (2016.02);
(Continued)

(58) Field of Classification Search
CPC .... A61M 2210/0681; A61M 2029/025; A61M 25/0082; A61M 25/0113;
(Continued)

(56) References Cited

U.S. PATENT DOCUMENTS

| 2,525,183 A | 10/1950 | Robison |
|---|---|---|
| 3,800,788 A | 4/1974 | White |

(Continued)

FOREIGN PATENT DOCUMENTS

| EP | 1 129 634 A1 | 1/1985 |
|---|---|---|
| EP | 159815 A1 | 11/2005 |

(Continued)

OTHER PUBLICATIONS

Iro, H., J. Zenk, "A new device for frontal sinus endoscopy: First Clinical Report", Department of Otorhinolaryngology, University of Eralngen-Nuremberg, Germany. Otorhinolaryngology, Head and Neck Surgery vol. 125 No. 6, Dec. 2001, pp. 613-616 (4 pages).

(Continued)

*Primary Examiner* — Martin T Ton
(74) *Attorney, Agent, or Firm* — McDonnell Boehnen Hulbert & Berghoff LLP

(57) ABSTRACT

A balloon dilation catheter includes a substantially rigid inner guide member and a movable shaft coupled to a balloon that is slidably mounted on the substantially rigid inner guide member. To treat a sinus cavity of a subject using the balloon dilation the substantially rigid inner guide member is advanced into a drainage pathway of the sinus (e.g., frontal recess) of the subject via a nasal passageway. The shaft and balloon are advanced in a distal direction over the substantially rigid inner guide member to place the balloon in the drainage pathway. The balloon is inflated to expand or otherwise remodel the drainage pathway.

16 Claims, 9 Drawing Sheets

Related U.S. Application Data

No. 14/524,889, filed on Oct. 27, 2014, now Pat. No. 9,339,637, which is a continuation of application No. 13/644,538, filed on Oct. 4, 2012, now Pat. No. 8,882,795, which is a continuation of application No. 13/116,712, filed on May 26, 2011, now Pat. No. 8,986,340, which is a continuation of application No. 12/479,521, filed on Jun. 5, 2009, now Pat. No. 8,282,667.

(51) Int. Cl.
 *A61B 34/30* (2016.01)
 *A61B 34/20* (2016.01)
 *A61M 25/01* (2006.01)
 *A61M 25/10* (2013.01)

(52) U.S. Cl.
 CPC ........ *A61M 25/0113* (2013.01); *A61M 25/10* (2013.01); *A61B 2017/246* (2013.01)

(58) Field of Classification Search
 CPC .. A61M 2025/0004; A61M 2025/0006; A61M 2025/0681; A61M 2210/0618; A61M 25/10; A61B 17/24; A61B 2017/246
 USPC .............. 606/196, 199; 604/103.03, 117
 See application file for complete search history.

(56) References Cited

U.S. PATENT DOCUMENTS

| | | | |
|---|---|---|---|
| 3,861,393 A | 1/1975 | Durand | |
| 4,566,438 A * | 1/1986 | Liese ............... | A61B 5/6848 600/129 |
| 4,737,141 A | 4/1988 | Spits | |
| 5,024,658 A | 6/1991 | Kozlov et al. | |
| 5,021,043 A | 7/1991 | Becker et al. | |
| 5,169,386 A | 12/1992 | Becker et al. | |
| 5,195,989 A | 3/1993 | Euteneuer | |
| 5,324,257 A | 6/1994 | Osborne | |
| 5,391,199 A | 2/1995 | Ben-Haim | |
| 5,415,634 A | 5/1995 | Glynn et al. | |
| 5,441,497 A * | 8/1995 | Narciso, Jr. ......... | A61B 18/245 606/15 |
| 5,443,489 A | 8/1995 | Ben-Haim | |
| 5,466,222 A | 11/1995 | Ressemann et al. | |
| 5,470,315 A | 11/1995 | Adams | |
| 5,569,274 A | 10/1996 | Rapacki et al. | |
| 5,588,950 A | 12/1996 | Sano et al. | |
| 5,632,762 A | 5/1997 | Myler | |
| 5,645,628 A | 7/1997 | Thome | |
| 5,795,325 A | 8/1998 | Valley et al. | |
| 5,964,767 A | 10/1999 | Tapia et al. | |
| 6,083,188 A | 7/2000 | Becker | |
| 6,090,132 A | 7/2000 | Fox | |
| 6,113,567 A | 9/2000 | Becker | |
| 6,206,870 B1 | 3/2001 | Kanner | |
| 6,238,364 B1 | 5/2001 | Becker | |
| 6,491,940 B1 | 12/2002 | Levin | |
| 6,543,452 B1 | 4/2003 | Lavigne | |
| D501,677 S | 2/2005 | Becker | |
| 6,851,424 B2 | 2/2005 | Scopton | |
| 7,500,971 B2 | 3/2009 | Chang et al. | |
| 7,520,876 B2 | 4/2009 | Ressemann et al. | |
| 7,678,099 B2 | 3/2010 | Ressemann et al. | |
| 7,785,315 B1 | 8/2010 | Muni et al. | |
| 7,842,062 B2 | 11/2010 | Keith et al. | |
| 7,879,061 B2 | 2/2011 | Keith et al. | |
| 7,918,871 B2 | 4/2011 | Truitt et al. | |
| 8,114,113 B2 * | 2/2012 | Becker ................ | A61M 3/0295 606/196 |
| 8,146,400 B2 | 4/2012 | Goldfarb et al. | |
| 8,241,266 B2 | 8/2012 | Keith et al. | |
| 8,277,478 B2 | 10/2012 | Drontle et al. | |
| 8,282,667 B2 | 10/2012 | Drontle et al. | |
| 8,348,969 B2 | 1/2013 | Keith et al. | |
| 8,568,439 B2 | 10/2013 | Keith et al. | |
| 8,585,728 B2 | 11/2013 | Keith et al. | |
| 8,585,729 B2 | 11/2013 | Keith et al. | |
| 8,623,043 B1 | 1/2014 | Keith et al. | |
| 8,657,846 B2 | 2/2014 | Keith et al. | |
| 8,801,670 B2 | 8/2014 | Drontle et al. | |
| 8,834,513 B2 | 9/2014 | Hanson et al. | |
| 8,882,795 B2 | 11/2014 | Drontle et al. | |
| 8,888,686 B2 | 11/2014 | Drontle et al. | |
| 8,915,938 B2 | 12/2014 | Keith et al. | |
| 8,986,340 B2 | 3/2015 | Drontle et al. | |
| 9,005,284 B2 | 4/2015 | Ressemann | |
| 9,011,412 B2 | 4/2015 | Albritton, IV et al. | |
| 9,101,739 B2 | 8/2015 | Lesch, Jr. et al. | |
| 9,192,748 B2 | 11/2015 | Ressemann et al. | |
| 9,278,199 B2 | 3/2016 | Keith et al. | |
| 9,282,986 B2 | 3/2016 | Hanson | |
| 9,283,360 B2 | 3/2016 | Lesch et al. | |
| 9,320,876 B2 | 4/2016 | Ressemann et al. | |
| 9,333,327 B2 | 5/2016 | Setliff, III et al. | |
| 9,339,637 B2 | 5/2016 | Drontle et al. | |
| 9,370,650 B2 | 6/2016 | Hanson | |
| 9,433,343 B2 | 9/2016 | Drontle et al. | |
| 9,440,049 B2 | 9/2016 | Drontle et al. | |
| 94,333,343 | 9/2016 | Drontle et al. | |
| 9,486,614 B2 | 11/2016 | Drontle et al. | |
| 9,550,049 B2 | 1/2017 | Hanson | |
| 9,694,167 B2 | 7/2017 | Keith et al. | |
| 9,700,705 B2 | 7/2017 | Lesch, Jr. et al. | |
| 9,775,975 B2 | 10/2017 | Ressemann et al. | |
| 10,022,525 B2 | 7/2018 | Hanson et al. | |
| 10,029,069 B2 | 7/2018 | Keith et al. | |
| 10,086,181 B2 | 10/2018 | Lesch et al. | |
| 2002/0065455 A1 | 5/2002 | Ben-Haim et al. | |
| 2002/0138121 A1 | 9/2002 | Fox | |
| 2004/0054349 A1 * | 3/2004 | Brightbill ......... | A61M 25/0012 604/524 |
| 2004/0064083 A1 | 4/2004 | Becker | |
| 2004/0064150 A1 | 4/2004 | Becker | |
| 2004/0068299 A1 | 4/2004 | Laske et al. | |
| 2005/0059931 A1 | 3/2005 | Garrison et al. | |
| 2005/0075661 A1 | 4/2005 | Levine et al. | |
| 2005/0240147 A1 | 10/2005 | Makower et al. | |
| 2005/0245906 A1 | 11/2005 | Makower et al. | |
| 2005/0251119 A1 | 11/2005 | Eaton et al. | |
| 2006/0004286 A1 | 1/2006 | Chang et al. | |
| 2006/0004323 A1 | 1/2006 | Chang et al. | |
| 2006/0063973 A1 | 3/2006 | Makower et al. | |
| 2006/0095066 A1 | 5/2006 | Chang et al. | |
| 2006/0100687 A1 | 5/2006 | Fahey et al. | |
| 2006/0106361 A1 | 5/2006 | Muni et al. | |
| 2006/0111691 A1 | 5/2006 | Bolmsjo et al. | |
| 2006/0149310 A1 | 7/2006 | Becker | |
| 2006/0210605 A1 | 9/2006 | Chang et al. | |
| 2006/0284428 A1 | 12/2006 | Beadle et al. | |
| 2006/0293612 A1 | 12/2006 | Jenson et al. | |
| 2007/0005094 A1 | 1/2007 | Eaton et al. | |
| 2007/0073269 A1 | 3/2007 | Becker | |
| 2007/0129751 A1 | 6/2007 | Muni et al. | |
| 2007/0135789 A1 | 6/2007 | Chang et al. | |
| 2007/0135803 A1 | 6/2007 | Belson | |
| 2007/0167682 A1 | 7/2007 | Goldfarb et al. | |
| 2007/0208252 A1 | 9/2007 | Makower | |
| 2007/0208301 A1 | 9/2007 | Evard et al. | |
| 2007/0249896 A1 | 10/2007 | Goldfarb et al. | |
| 2007/0250105 A1 | 10/2007 | Ressemann et al. | |
| 2007/0270644 A1 | 11/2007 | Goldfarb et al. | |
| 2007/0282305 A1 | 12/2007 | Goldfarb et al. | |
| 2007/0293726 A1 | 12/2007 | Goldfarb et al. | |
| 2007/0293727 A1 | 12/2007 | Goldfarb et al. | |
| 2008/0015472 A1 | 1/2008 | Ressemann et al. | |
| 2008/0015540 A1 | 1/2008 | Muni et al. | |
| 2008/0033353 A1 | 2/2008 | Truitt et al. | |
| 2008/0082045 A1 | 4/2008 | Goldfarb et al. | |
| 2008/0097154 A1 | 4/2008 | Makower et al. | |
| 2008/0097239 A1 | 4/2008 | Chang et al. | |
| 2008/0097295 A1 | 4/2008 | Makower et al. | |
| 2008/0097400 A1 | 4/2008 | Chang et al. | |

(56) References Cited

U.S. PATENT DOCUMENTS

| | | |
|---|---|---|
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0154217 A1* | 6/2008 | Carrez .............. A61L 27/14 604/272 |
| 2008/0154237 A1 | 6/2008 | Chang et al. |
| 2008/0154250 A1 | 6/2008 | Makower et al. |
| 2008/0172033 A1 | 7/2008 | Keith et al. |
| 2008/0195041 A1 | 8/2008 | Goldfarb et al. |
| 2008/0228085 A1 | 9/2008 | Jenkins et al. |
| 2008/0234720 A1 | 9/2008 | Chang et al. |
| 2008/0269596 A1 | 10/2008 | Revie et al. |
| 2008/0275483 A1 | 11/2008 | Makower et al. |
| 2008/0281156 A1 | 11/2008 | Makower et al. |
| 2008/0287908 A1* | 11/2008 | Muni ................. A61B 17/24 604/506 |
| 2008/0319424 A1 | 12/2008 | Muni et al. |
| 2009/0005763 A1 | 1/2009 | Makower et al. |
| 2009/0028923 A1 | 1/2009 | Muni et al. |
| 2009/0030274 A1 | 1/2009 | Goldfarb et al. |
| 2009/0030380 A1* | 1/2009 | Binmoeller .......... A61B 1/018 604/264 |
| 2009/0073718 A1 | 3/2009 | Chung |
| 2009/0093823 A1 | 4/2009 | Chang et al. |
| 2009/0132033 A1 | 5/2009 | Maurer et al. |
| 2009/0187098 A1 | 7/2009 | Makower et al. |
| 2009/0198216 A1 | 8/2009 | Muni et al. |
| 2009/0204142 A1 | 8/2009 | Becker |
| 2009/0216196 A1 | 8/2009 | Drontle et al. |
| 2009/0318875 A1* | 12/2009 | Friedman .......... A61B 17/3468 604/187 |
| 2010/0016811 A1* | 1/2010 | Smith ............... A61B 17/3417 604/273 |
| 2010/0030113 A1 | 2/2010 | Morriss et al. |
| 2010/0168511 A1 | 7/2010 | Muni et al. |
| 2010/0211007 A1 | 8/2010 | Lesch et al. |
| 2010/0241155 A1 | 9/2010 | Chang et al. |
| 2010/0274222 A1 | 10/2010 | Setliff, III et al. |
| 2010/0312101 A1 | 12/2010 | Drontle |
| 2011/0071349 A1 | 3/2011 | Drontle et al. |
| 2011/0224652 A1 | 9/2011 | Drontle et al. |
| 2012/0010646 A1 | 1/2012 | Keith et al. |
| 2012/0184983 A1 | 7/2012 | Chang et al. |
| 2012/0283625 A1 | 11/2012 | Keith et al. |
| 2013/0030458 A1 | 1/2013 | Drontle et al. |
| 2013/0030459 A1 | 1/2013 | Drontle et al. |
| 2013/0041463 A1 | 2/2013 | Ressemann |
| 2013/0072958 A1 | 3/2013 | Ressemann et al. |
| 2013/0123833 A1 | 5/2013 | Lesch et al. |
| 2014/0350520 A1 | 11/2014 | Drontle et al. |
| 2014/0357959 A1 | 12/2014 | Hanson et al. |
| 2014/0364700 A1 | 12/2014 | Hanson et al. |
| 2014/0378776 A1 | 12/2014 | Hanson et al. |
| 2015/0031950 A1 | 1/2015 | Drontle et al. |
| 2015/0105818 A1 | 4/2015 | Keith et al. |
| 2016/0038726 A1 | 2/2016 | Hanson et al. |
| 2016/0151614 A1 | 6/2016 | Ressemann et al. |
| 2016/0166814 A1 | 6/2016 | Lesch et al. |
| 2016/0367286 A1 | 12/2016 | Drontle et al. |
| 2016/0375229 A1 | 12/2016 | Setfliff, III et al. |
| 2017/0007282 A1 | 1/2017 | Drontle |
| 2017/0028112 A1 | 2/2017 | Drontle et al. |
| 2017/0050001 A1 | 2/2017 | Drontle et al. |
| 2017/0113027 A1 | 4/2017 | Drontle et al. |
| 2017/0368319 A1 | 12/2017 | Lesch, Jr. et al. |
| 2018/0008806 A1 | 1/2018 | Ressemann et al. |
| 2018/0304051 A1 | 10/2018 | Keith et al. |
| 2018/0304058 A1 | 10/2018 | Hanson et al. |

FOREIGN PATENT DOCUMENTS

| | | |
|---|---|---|
| JP | 2009-505691 A | 2/2009 |
| WO | WO 91/177787 A1 | 11/1991 |
| WO | WO 96/00033 A1 | 1/1996 |
| WO | WO 2005/086945 A2 | 9/2005 |
| WO | WO 2007/035204 A2 | 3/2007 |
| WO | WO 2009/065085 A1 | 5/2009 |
| WO | WO2010/014799 A1 | 2/2010 |
| WO | 2017/135980 A1 | 8/2017 |
| WO | 2017/192394 A1 | 11/2017 |

OTHER PUBLICATIONS

Petersen, Robert J., Canine Fossa Puncture, The Laryngoscope Office, Oct. 5, 1972, pp. 369-371.

Elidan, J., MD., Irrigation of the Maxillary Sinus by Canine Fossa Puncture Experience with 202 Patients, Ann Otol Rhinol Laryngol, 92:1983, pp. 528-529.

Yanagisawa, Eiji, et al., Trans-Canine-Fossa Maxillary Sinoscopy for Biopsy Via the Stammberger Technique, ENT Rhinoscopic Clinic, Aug. 2001 Rhino, pp. 1-3.

Yanagisawa, Eiji, et al., Powered Endoscopic Inferior Meatal Antrostomy Under Canine Fossa Telescopic Guidance, ENT-Ear, Nose & Throat Journal, Sep. 2001, pp. 618-620.

Sathananthar, Shanmugam, et al., Canine Fossa Puncture and Clearance of the Maxillary Sinus for the Severely Diseased Maxillary Sinus, The Laryngoscope 115: Jun. 2005, pp. 1026-1029.

Robinson, Simon, et al., Patterns of Innervation of the Anterior Maxilla: A Cadaver Study with Relevance to Canine Fossa Puncture of the Maxillary Sinus, Laryngoscope 115: Oct. 2005, pp. 1785-1788.

Bolger, William, E., et al., Catheter-Based Dilation of the Sinus Ostia: Initial Safety and Feasibility Analysis in a Cadaver Model, Maryland Sinus Clinic, Bethesda, Maryland, and California Sinus Institute, Palo Alto, California, OceanSide Publications, Inc., May-Jun. 2006, vol. 20, No. 3, pp. 290-294.

Friedman, Michael, M.D. et al., Functional Endoscopic Dilatation of the Sinuses (FEDS): Patient Selection and Surgical Technique, Operative Technologies in Otolaryngology, vol. 17, No. 2, Jun. 2006, pp. 126-134.

Jones, Nick, Commentary on "Safety and Feasibility of Balloon Catheter Dilation of Paranasal Sinus Ostia: A Preliminary Investigation", Annals of Otology, Rhinology & Laryngology 115(4), pp. 300-301 (2006).

Bolger, William E., Commentary Misconceptions Regarding Balloon Catheter Dilation of Paranasal Sinus Ostia, Annals of Otology, Rhinology & Laryngology 115(10): 791-792 (2006).

Lanza, Donald, C., et al., Commentary Balloon Sinuplasty: Not Ready for Prime Time, Annals of Otology, Rhinology & Laryngology 115(10): 789-790 (2006).

Brown, Christopher, L., et al., "Safety and Feasibility of Balloon Catheter Dilation of Paranasal Sinus Ostia: A Preliminary Investigation", Annals of Otology, Rhinology & Laryngology 115(4):293-299 (2006).

Gottman, D., et al., "Balloon Dilatation of Recurrent Ostia Occlusion of the Frontal Sinus", ECR Mar. 3, 2001, 2:-3:30 PM, Vienna Austria (1 page).

Entellus Medical, 510(k) Premarket Notification cover letter and Attachment B: Predicate Device Labeling, dated Aug. 15, 2007.

R. Peterson, Sinus Puncture Therreapy: Canine Fossa Puncture Method "How I Do It" Head and Neck, The Larynsgoscope 91: Dec. 1981, pp. 2126-2128.

T.G.A. Ijaduola, Use of a Foley Catheter for Short-Tem Drainage of Frontal Sinus Surgery, Journ. of Laryngology and Otology, Apr. 1989, vol. 103, pp. 375-378.

A. Gatot et al., Early Treatment of Oribital Floor Fractures with Catheter Balloon in Childre, Int'l. J. of Ped. Otorhinolaryngology, 21 (1991) 97-101.

D.I. Tarasov et al., Treatment of Chronic Ethmoiditis by IntraCellular Administration of Medicines to the Ethmoidal Labyrinth, Vestn Otorinolaringol. Nov.-Dec. 1978; (6):45-47 (Abstract in English).

(56) References Cited

OTHER PUBLICATIONS

J.M. Robison, Pressure Treatment of Maxillary Sinusitis, J.A.M.A., May 31, 1952, pp. 436-440.
J.M. Robison, Pressure Treatment of Purulent Maxillary Sinusitis, Texas State Journal of Medicine, May 1952, pp. 281-288.
Entellus Medical, 510(k) Letter (Amendment 1) and Attachment D&E, dated Mar. 13, 2008.
Gottman et al., Balloon Dilation of Recurrent Ostial Occlusion of the Frontal Sinus, Gottman et al.: Abstract (B-0453) Mar. 2001, 22 pages.
PCT International Search Report for PCT/US2007/088834, Applicant: Entellus Medical, Inc., Forms PCT/ISA/220 and PCT/ISA/210, dated May 20, 2008 (4 pages).
PCT Written Opinion for PCT/US2007/088834, Applicant: Entellus Medical, Inc., Forms PCT/ISA/237, dated May 20, 2008 (10 pages).
PCT International Search Report for PCT/US2007/66187, Applicant: Entellus Medical, Inc., Forms PCT/ISA/220 and PCT/ISA/210, dated Apr. 17, 2008 (5 pages).
PCT Written Opinion for PCT/US2007/66187, Applicant: Entellus Medical, Inc., Forms PCT/ISA/237, dated Apr. 17, 2008 (5 pages).
Folweiler, David S., Nasal Specific Technique as Part of a Chropractic Approach to Chronic Sinusitis and Sinus Headaches, Journal of Manipulative and Physiological Therapeutics, vol. 18, No. 1 (Jan. 1995).
PCT International Preliminary Report on Patentability (Chapter I of the Patent Cooperation Treaty) of the International Bureau for PCT/US2007/066187, Applicant: Entellus Medical, Inc., Form PCT/IB/326, dated Oct. 30, 2006 (4 pages).
Medtronic, ENT Image-Guided Surgery System, http://www.xomed.com/xomed_products_element.html, Jun. 3, 2009 (2 pages).
International Search Report dated Aug. 2, 2010, for PCT/US2010/037508, Applicant: Entellus Medical, Inc. (4 pages).
Written Opinion of the International Search Authority dated Aug. 2, 2010, for PCT/US2010/037508, Applicant: Entellus Medical, Inc. (4 pages).
International Preliminary Report on Patentability dated Jul. 30, 2009, for PCT/US2007/088834, Applicant: Entellus Medical, Inc. (9 pages).
PCT International Preliminary Report on Patentability (Chapter I of the Patent Cooperation Treaty) for PCT/US2010/037508, Applicant: Entellus Medical Inc., Form PCT/IB/326 and 373, dated Dec. 15, 2011 (6pages).
Extended European Search Report dated Oct. 23, 2012 issued by the European Patent Office in EP Application No. 10784199.1-1526 /2437843 PCT/US2010037508, Applicant: Entellus Medical, Inc., (6pages).
Notification of First Office Action dated Apr. 2, 2013 issued by the Chinese Patent Office in Chinese Patent Application No. 201080024851.X, Applicant: Entellus Medical, Inc., (7pages), including an English translation prepared by Kangxin Partners, P.C. (7pages).
Communication under Rule 71(3) EPC issued by the European Patent Office dated May 21, 2015 in European Patent Application No. 10 784 199.1-1506, Applicant: Entellus Medical, Inc., (6pages).
Notification of the Second Office Action issued by the The State Intellectual Property Office of P.R.C. dated Dec. 25, 2013 in Chinese Patent Application No. 201080024851.X including English Translation prepared by Kangxin Partners, Applicant: Entellus Medical, Inc., (5pages).
Notification of the Third Office Action issued by the The State Intellectual Property Office of P.R.C. dated Jul. 15, 2014 in Chinese Patent Application No. 201080024851.X including English Translation prepared by Kangxin Partners, Applicant: Entellus Medical, Inc., (8pages).
Notice of Rejection issued by the Japanese Patent Office dated Mar. 18, 2014 in Japanese Patent Application No. 2012-514199 including English Translation prepared by Kita-Aoyama International Patent Bureau, Applicant: Entellus Medical, Inc., (4pages).
Decision of Rejection issued by the Japanese Patent Office dated Sep. 2, 2014 in Japanese Patent Application No. 2012-514199 including English Translation prepared by Kita-Aoyama International Patent Bureau, Applicant: Entellus Medical, Inc., (3pages).
Notice of Allowance issued by the Japanese Patent Office dated May 12, 2015 in Japanese Patent Application No. 2012-514199 including English Translation prepared by Kita-Aoyama International Patent Bureau, Applicant: Entellus Medical, Inc., (4pages).
The extended European search report dated Jan. 21, 2016 in European Application No. 15184180.6-1501, (6pages).
Communication pursuant to Article 94(3) EPC dated May 4, 2018 in European Patent Application No. 15184180.6-1132, Applicant: Entellus Medical, Inc., (4pages).
Office Action dated Jun. 1, 2018 in U.S. Appl. No. 15/139,052, (44pages).
Fiber-optic Surgical Probe, http://www.anthonyproducts.com/store/p-389-fiber-optic-surgical-probe.aspx, 1 page, at least as early as Jul. 12, 2011.
Light Probe Kit, http://www.fiberoptix.com/products/light-probe-kit.html, 2 pages, Apr. 2010.

\* cited by examiner

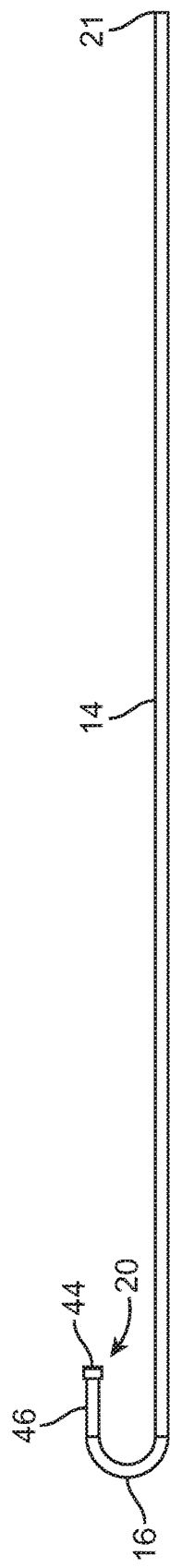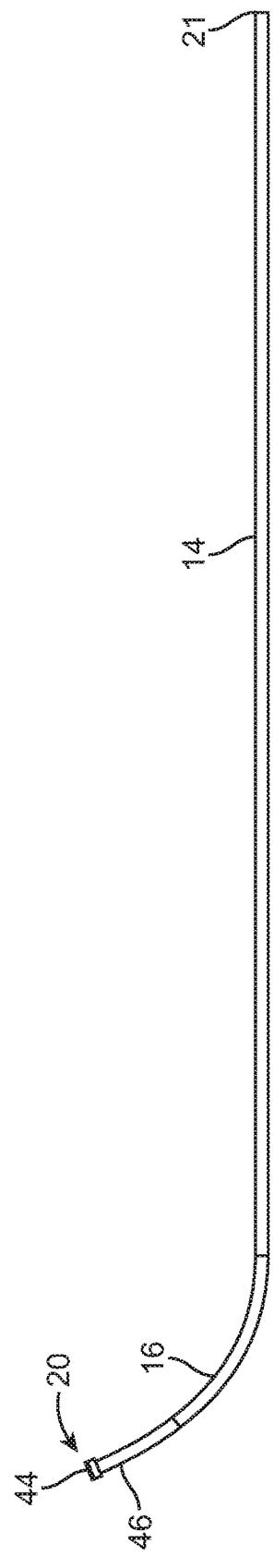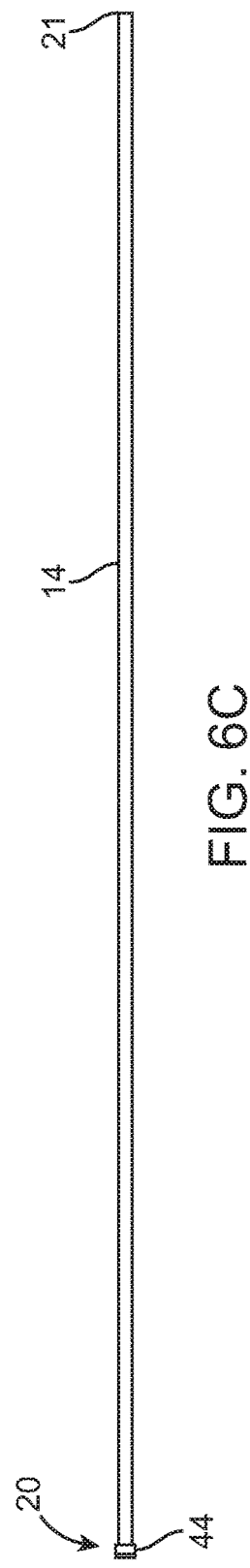

SINUS DILATION CATHETER

RELATED APPLICATIONS DATA

Application is a continuation of U.S. patent application Ser. No. 15/139,052 filed on Apr. 26, 2016, which itself is a continuation of U.S. patent application Ser. No. 14/524,889, filed on Oct. 27, 2014, now issued as U.S. Pat. No. 9,339,637, which itself is a continuation of U.S. application Ser. No. 13/644,538, filed on Oct. 4, 2012, now U.S. Pat. No. 8,882,795, which is a continuation of U.S. patent application Ser. No. 13/116,712 filed on May 26, 2011, which is a continuation of U.S. application Ser. No. 12/479,521, filed on Jun. 5, 2009, now U.S. Pat. No. 8,282,667. The above-noted Applications are incorporated by reference as if set forth fully herein.

FIELD OF THE INVENTION

The field of the invention generally relates to balloon inflation devices and methods. More particularly, the field of the invention relates to balloon dilation devices and methods for the treatment of sinusitis.

BACKGROUND OF THE INVENTION

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed, or otherwise has compromised drainage. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has a drainage pathway or outflow tract opening into the nasal passage. This drainage passageway can include an ostium, as well as a "transition space" in the region of the ostia, such as the "frontal recess," in the case of the frontal sinus, or an "ethmoidal infundibulum," in the case of the maxillary sinus. When the mucosa of one or more of the ostia or regions near the ostia become inflamed, the egress of mucous is interrupted, setting the stage for an infection and/or inflammation of the sinus cavity, i.e., sinusitis. Though many instances of sinusitis may be treatable with appropriate medicates, in some cases sinusitis persists for months or more, a condition called chronic sinusitis, and may not respond to medical therapy. Some patients are also prone to multiple episodes of sinusitis in a given period of time, a condition called recurrent sinusitis.

Balloon dilation has been applied to treat constricted sinus passageways for the treatment of sinusitis. These balloon dilation devices typically involve the use of an inflatable balloon located at the distal end of a catheter such as a balloon catheter. Generally, the inflatable balloon is inserted into the constricted sinus passageway in a deflated state. The balloon is then expanded to open or reduce the degree of constriction in the sinus passageway being treated to facilitate better sinus drainage and ventilation. At the same time most, if not all, of the functional mucosal tissue lining of the sinuses and their drainage passageways are preserved.

Exemplary devices and methods particularly suited for the dilation of anatomic structures associated with the maxillary and anterior ethmoid sinuses are disclosed, for example, in U.S. Pat. No. 7,520,876 and U.S. Patent Application Publication No. 2008-0172033. Other systems have been described for the treatment of various other sinuses including the frontal sinus. For example, U.S. Patent Application Publication No. 2008-0097295 discloses a frontal sinus guide catheter (FIG. 6B) and method of treating the frontal sinuses (e.g., FIGS. 8B-8C). U.S. Patent Application Publication No. 2008-0125626 discloses another guide device (e.g., FIGS. 10C and 10C') for transnasal access to the frontal sinuses for treatment.

SUMMARY OF THE INVENTION

In a first embodiment of the invention, a balloon dilation catheter includes a substantially rigid inner guide member and a movable shaft coupled to a balloon that is slidably mounted on the substantially rigid inner guide member. To treat a drainage pathway of a sinus cavity (e.g., frontal sinus cavity) of a subject using the balloon dilation catheter, the substantially rigid inner guide member is advanced into a drainage pathway of the subject via a nasal passageway. The shaft and balloon are then advanced in a distal direction over the substantially rigid inner guide member to place the balloon in the drainage pathway. This enables the balloon to track over the inner guide member. The balloon is inflated to expand or otherwise remodel the drainage pathway. Where the sinus cavity is the frontal sinus cavity the drainage pathway is the frontal recess.

In another aspect of the invention, a device for dilating the outflow tract of a sinus cavity includes a substantially rigid inner guide member having a proximal end and a distal end and a shaft coupled to a balloon, the shaft having a first lumen along at least a portion thereof containing the substantially rigid inner guide member, the shaft having a second lumen operatively coupled to the interior of the balloon. A handle is disposed along a proximal portion of the substantially rigid inner guide member, the handle including a moveable knob operatively coupled to the shaft, wherein distal advancement of the knob advances the shaft and balloon over the substantially rigid inner guide in a distal direction.

BRIEF DESCRIPTION OF THE DRAWINGS

FIG. 6A is a side view of an inner guide member according to one embodiment.

FIG. 6B is a side view of an inner guide member according to another embodiment.

FIG. 6C is a side view of an inner guide member according to another embodiment.

DETAILED DESCRIPTION OF THE ILLUSTRATED EMBODIMENTS

Figure 1:
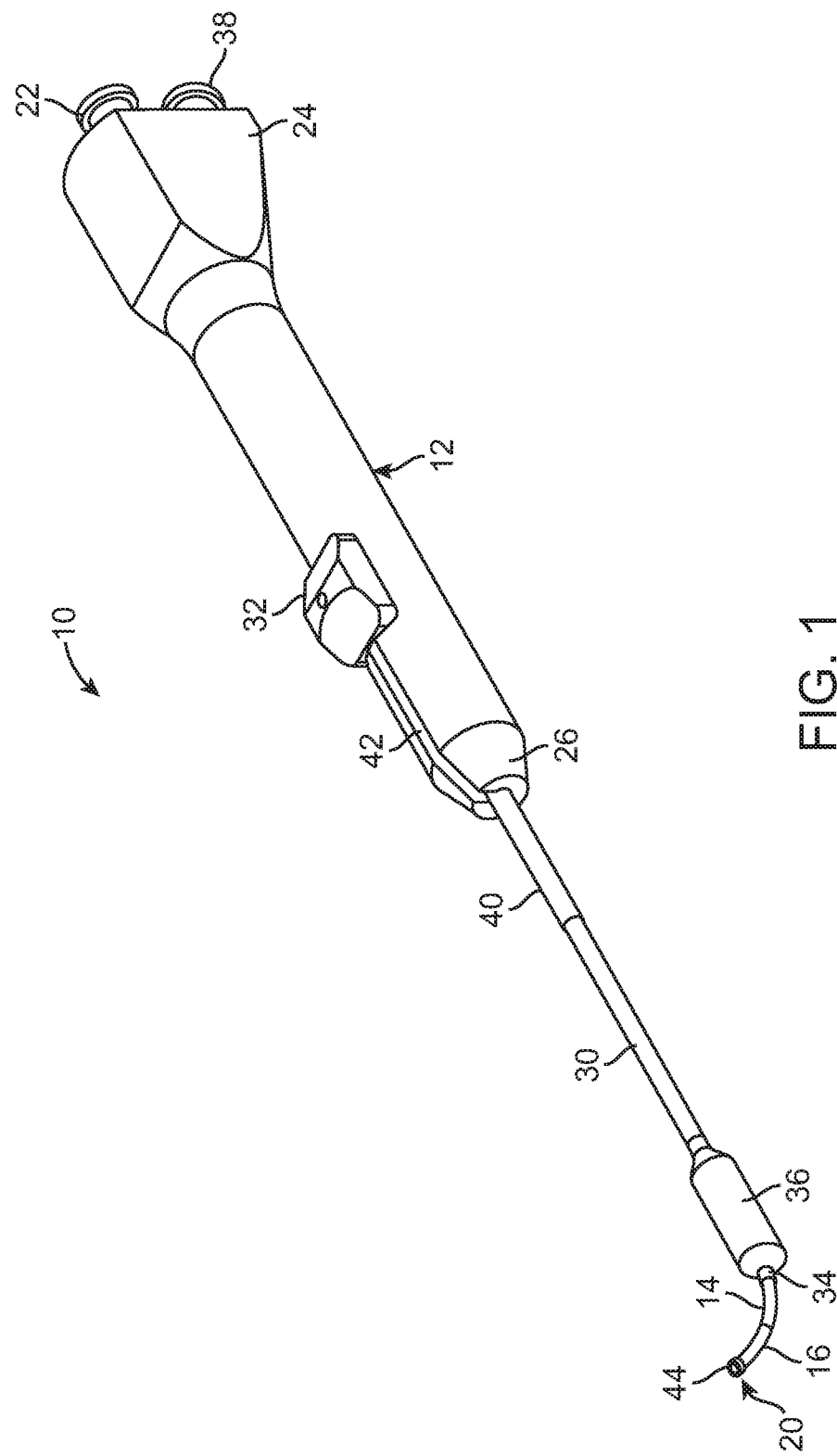
FIG. 1 illustrates a perspective view of a balloon dilation catheter according to one embodiment.

FIG. 1 illustrates one embodiment of a balloon dilation catheter 10 that is particularly suited for treatment of the outflow tract (frontal sinus ostium and frontal recess) of the frontal sinus of a subject. The balloon dilation catheter 10 includes a handle 12 that is configured to be gripped or otherwise manipulated by the operator. An elongate-shaped inner guide member 14 extends longitudinally from the handle 12 in a distal direction. The inner guide member 14 is formed of a suitably rigid material such as stainless steel hypotube. The inner guide member 14 projects or otherwise extends distally from the handle 12 for a pre-determined distance. The inner guide member 14 may be pre-shaped to have a curved distal portion 16 as is illustrated in FIGS. 1, 2A, 2B, 3A, 3B, 6A, 6B, 7, 8, and 9. For example, the nature and degree of the curved distal portion 16 may be configured to match with the frontal sinus outflow tract or frontal recess.

Alternatively, the inner guide member 14 may have some degree of malleability such that the user may bend or impart some desired shape or configuration to the distal end of the inner guide member 14. As explained herein in more detail, the inner guide member 14 may include an optional lumen 18 (best illustrated in FIG. 5A) that extends the length of the inner guide member 14. In particular, the inner guide member 14 and the contained lumen 18 may extend from a distal end 20 to a proximal end 21 (best seen in FIGS. 2B and 3B) that interfaces with a sealed arrangement with a port 22 disposed at a proximal end 24 of the handle 12. The port 22 may be configured with a conventional interface such as a Luer connector. The port 22 may be used as an aspiration port or a delivery port for fluids and/or medicaments, or for introduction of a guide wire.

Figure 2A:
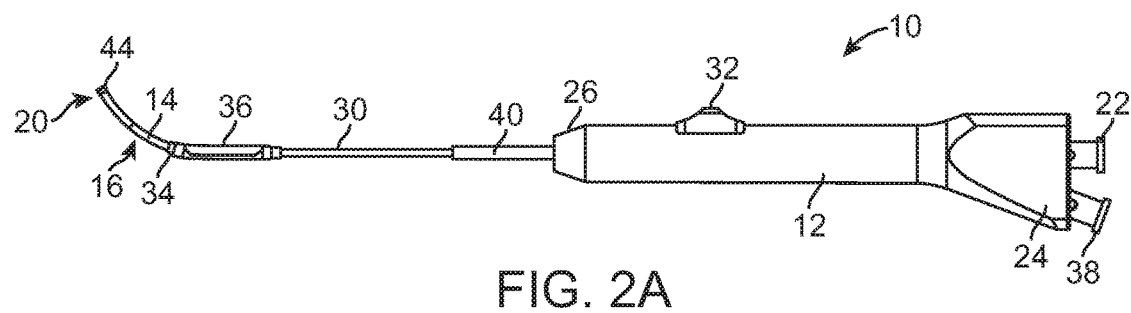
FIG. 2A illustrates a side view of a balloon dilation catheter of FIG. 1. The advancer knob is illustrated in the retracted, proximal position.
Figure 2B:
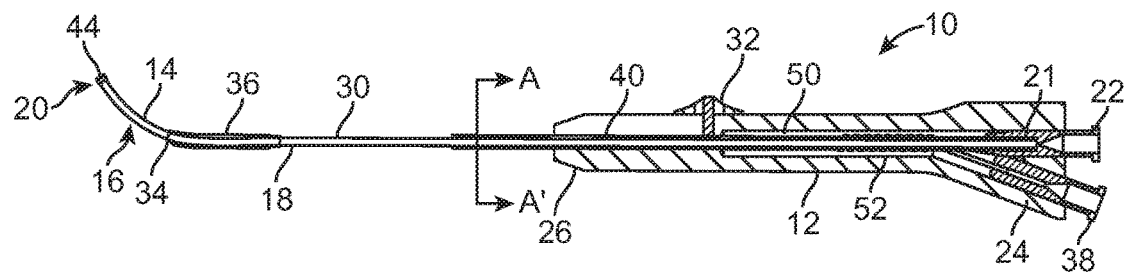
FIG. 2B illustrates a cross-sectional view of the balloon dilation catheter of FIG. 2A.

Still referring to FIG. 1, a shaft 30 is mounted about the periphery of the inner guide member 14. In particular, the shaft 30 is dimensioned to slide over the inner guide member 14 in response to actuation of an advancer knob 32 located on the handle 12. The advancer knob 32 is moveable along a slot 42 contained in a surface of the handle 12. A distal end 34 of the shaft 30 includes a balloon 36 that is configured to be selectively inflated or deflated as explained herein. During use, the inner guide member 14 is manipulated and advanced across or into the anatomical space of interest. The shaft 30 as well as the attached balloon 36 is illustrated in a retracted state in FIG. 1. While FIG. 1 illustrates the balloon 36 in an inflated state for better illustration, the balloon 36 is typically in a deflated state when the shaft 30 is in the proximal position as illustrated in FIGS. 2A and 2B. After the inner guide member 14 is properly positioned, the user actuates the advancer knob 32 by sliding the same in the distal direction which, in turn, advances the shaft 30 and balloon 36 in a distal direction over the pre-placed inner guide member 14. Once the balloon 36 is properly placed, the balloon 36 is inflated. Inflation of the balloon 36 is accomplished using an inflation device (not shown) that is coupled to a port 38 located at the proximal end 24 of the handle 12. One exemplary inflation device that may be used in connection with the balloon dilation catheter 10 is described in U.S. Patent Application Publication No. 2010-0211007, which is incorporated by reference as if set forth fully herein. Of course, other inflation devices may also be used. An inflation lumen 48 contained within the shaft 30 (described in more detail below), fluidically couples the port 38 to an interior portion of the balloon 36.

Still referring to FIG. 1, an optional support member 40 in the form of a tube may be located about the external periphery of a portion of the shaft 30 to impart further stiffness to the balloon dilation catheter 10. The particular length of the support member 40 may vary depending on the application and may extend along some or all or the shaft 30. The support member 40 may be made of a metallic material such as stainless steel hypotube that is secured to the shaft 30. The support member 40 may be welded or bonded along a length of the shaft 30. Generally, the support member 40 does not cover the helical portion (described in detail below) of the shaft 30 that is contained within the handle 12.

FIGS. 2A and 2B illustrate, respectively, side and cross-sectional views of the balloon dilation catheter 10 with the advancer knob 32 and thus balloon 36 in the proximal position. In actual use, as explained herein, the balloon 36 is typically in a deflated state when the advancer knob 32 is the proximal position as illustrated in FIGS. 2A and 2B. As best seen in FIG. 1, the advancer knob 32 is slidably disposed along a length of the handle 12 inside a slot 42. The advancer knob 32 is thus able to slide back and forth in the distal/proximal direction along the length of the slot 42. The slot 42 may incorporate a stop or the like (not shown) to prevent the balloon 36 from being advance too far along the length of the inner guide member 14. The length of the slot 42 may be varied in different devices to adjust the length at which the balloon 36 may be advanced. Generally, the slot 42 has a length within the range of about 1 inch to about 2 inches although other dimensions may fall within the scope of the invention.

As seen in FIG. 2B, the advancer knob 32 may be directly coupled to the support member 40 that is mounted on the shaft 30. Alternatively, the advancer knob 32 may be coupled directly to the shaft 30. The advancer knob 32 may be configured or otherwise shaped to enable a finger of the user (e.g., index finger or thumb) to easily advance or retract the knob 32 along the slot 42 contained in the handle 12.

Figure 3A:
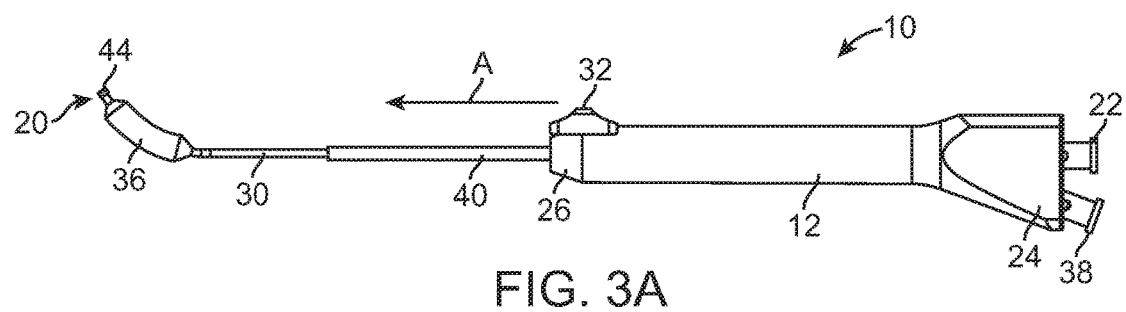
FIG. 3A illustrates a side view of a balloon dilation catheter of FIG. 1. The advancer knob is illustrated in the advanced, distal position.
Figure 3B:
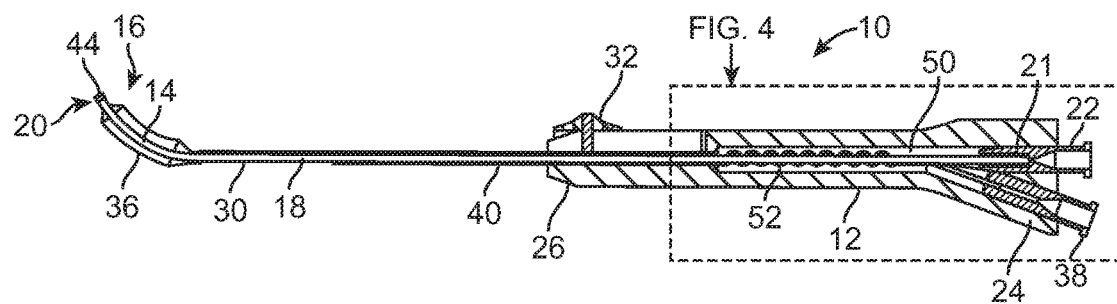
FIG. 3B illustrates a cross-sectional view of the balloon dilation catheter of FIG. 3A.

FIGS. 3A and 3B illustrate, respectively, side and cross-sectional views of the balloon dilation catheter 10 with the advancer knob 32 and thus balloon 36 in the distal position. Thus, unlike the configurations of FIGS. 2A and 2B, the advancer knob 32 is located at or near the distal end 26 of the handle 12. Advancement of the advancer knob 32 also slides the shaft 30 and attached balloon 36 in a distal direction (arrow A in FIG. 3A) along the inner guide member 14. The balloon 36 thus is positioned at or adjacent to the distal end 20 of the inner guide member 14. The balloon dilation catheter 10 may be designed such that the advancer knob 32 may be positioned at either the proximal or distal extremes as illustrated in FIGS. 2A, 2B, 3A, 3B. Alternatively, the advancer knob 32 may be positioned somewhere in between the two extremes. For example, the optimal position of the balloon 36 may be accomplished by sliding the advancer knob 32 some fraction (e.g., ¾) of the full distance of the slot 42.

Referring to FIGS. 2B and 3B, the inner guide member 14 of the balloon dilation catheter 10 extends from a distal end 20 to a proximal end 21 that terminates in a sealed interface with a port 22 disposed at a proximal end 24 of the handle 12. The inner guide member 14 optionally includes a lumen 18 disposed therein that may be used to provide aspiration functionality via an aspiration device (not shown) coupled to port 22. Aspiration functionality permits the removal of blood and other secretions. This makes it easier to visualize the placement of the balloon dilation catheter 10. The inner guide member 14 is advantageously rigid to enable the balloon dilation catheter 10 to be positioned without the need of a separate guiding catheter or guide wire in most, if not all, instances.

The inner guide member 14 may have a length of about 7 inches to about 11 inches from the distal end 20 to the proximal end 21 when loaded into the handle 12, although other dimensions may be used. The inner guide member 14 may be formed from stainless steel hypotube having an inner diameter in the range of about 0.020 inch to about 0.050 inch, and more preferably between about 0.036 inch and 0.040 inch, with a wall thickness within the range of about 0.005 inch to about 0.020 inch, and more preferably between about 0.008 inch to about 0.012 inch. The curved distal portion 16 of the inner guide member 14 may be formed right to the distal end 20 and may have a radius of curvature of about 0.25 inch to about 1.5 inch, and more preferably about 0.75 to about 1.25 inch.

The length of the inner guide member 14 that projects distally from the distal-most portion of the balloon 36 is about 0.5 inch to about 2.0 inch, and more preferably, about 0.8 inch to about 1.2 inch when the balloon 36 is in the fully retracted state (e.g., illustrated in FIGS. 2A and 2B). As seen in FIGS. 1, 2A, 2B, 3A, 3B, 6A-6C, 7-11, the distal end 20 of the inner guide member 14 may incorporate an optional bulbous tip 44 in order to make the distal end 20 more atraumatic. The bulbous tip 44 further serves to limit forward movement of the balloon 36 and attached shaft 30 when they are advanced distally. The outer diameter of the tip 44 is preferably between about 1 mm and about 3 mm.

The balloon 36 is mounted on the shaft 30 so as to form a fluidic seal between the two components. The balloon 36 may be bonded to the shaft using a weld, adhesive, or the like. Alternately, the balloon 36 may be secured to the shaft using a mechanical connection. Generally, any technique known to those skilled in the art may be used to secure to the balloon 36 to the shaft 30. Given that the balloon 36 is secured directly to the shaft 30, both structures are slidably mounted over the inner guide member 14. The balloon 36 generally takes on a cylindrical-shape when inflated. While not limited to specific dimensions, the inflated balloon 36 has a diameter within the range of about 3 mm to about 9 mm, and more preferably a diameter within the range of about 5 to about 7 mm when inflated. The length of the balloon 36 may generally fall within the range of about 10 mm to 25 mm although other lengths may be used. Both the shaft 30 and the balloon 36 are preferably formed of high strength but flexible polymeric materials such as polyamides (e.g., Nylon), PEBAX or the like. The balloon 36 may be "blow molded" to a relatively thin wall thickness, and capable of holding relatively high pressures from about 6 atmospheres to about 20 atmospheres of inflation pressure. The balloon 36 is inflated using a fluid which is typically a liquid such as water or saline.

Figure 4:
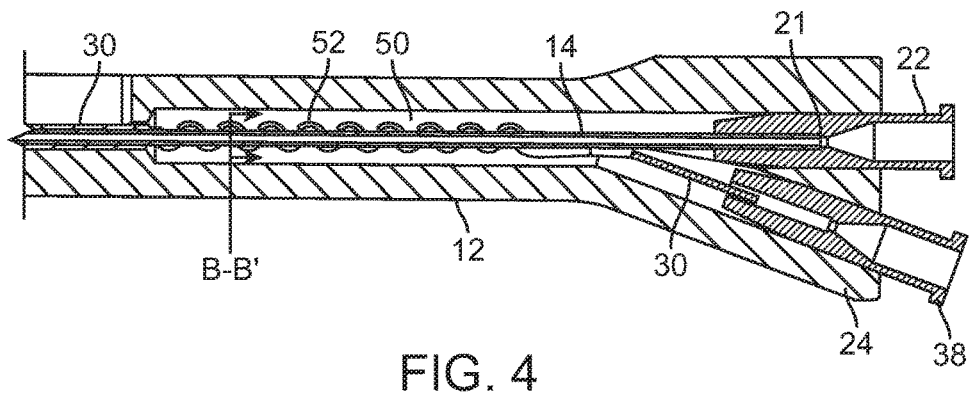
FIG. 4 is a cross-sectional view of the handle portion (dashed line portion) of FIG. 3B.

Referring now to FIG. 4, a magnified, cross-sectional view of a portion of the handle 12 is illustrated. At the proximal end 24 of the handle 12 are located ports 22, 38. The port 22 may be configured with a conventional interface such as a Luer connector or any other connector known to those skilled in the art. The port 22 may be integrally formed with the handle 12 or, alternatively, the port 22 may be a separate structure that is secured to the handle 12 during assembly. As seen in FIG. 4, the proximal end 21 of the inner guide member 14 forms a sealing arrangement with the port 22. As explained herein, the port 22 may be used as an aspiration port or a delivery port for fluids and/or medicaments.

FIG. 4 also illustrates port 38 which may be constructed in the same or similar manner as port 22 as described above. The port 38 is fluidically coupled to the inflation lumen 48 in the shaft 30. In this regard, inflation fluid from an inflation device (not shown) is able to pass through the port 38 and into the inflation lumen 48 of the shaft 30. The port 38 may be configured with a conventional interface such as a Luer connector. The fluid then is able to travel along the length of the shaft 30 via the lumen 48 where the fluid enters the interior of the balloon 36. The inflation fluid is thus able to inflate the balloon 36 upon actuation of the inflation device.

As best seen in FIG. 4, a portion of the handle 12 includes a recessed region 50 that receives both the inner guide member 14 and the shaft 30. In the recessed region 50 of the handle 12, the shaft 30 is helically wrapped around the outer periphery of the inner guide member 14 forming a helical portion 52. The helical portion 52 facilitates the distal advancement and proximal retraction of the shaft 30 and attached balloon 36 along the inner guide member 14 yet still maintains fluid communication with the port 38. The helical portion 52 of the shaft 30, which is located proximal to the advancer knob 32 is in the shape of a helix that wraps around the inner guide member 14 and is configured to elongate and contract upon movement of the advancer knob 32. FIG. 4 illustrates the state of the helical portion 52 after the advancer knob 32 has been advanced distally. Thus, in the extended state, the length of the helical portion 52 traverses much if not all of the recessed region 50. Contrast this with FIG. 2B which illustrates the helical portion 52 compressed to the proximal portion of the recessed region 50 because the advancer knob 32 is the in proximal position. Thus, the helical portion 52 is thus able to expand or compress much in the way that a spring does in response to a tensile or compressive load. One or both of the inner guide member 14 and the helical portion 52 of the shaft 30 may be optionally coated or lined with a lubricious coating to prevent the contact surfaces from any unwanted frictional binding or the like.

Figure 5A:
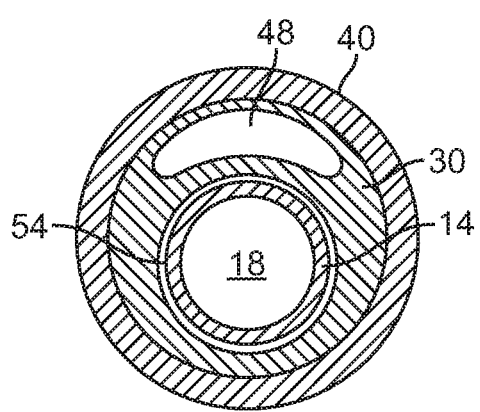
FIG. 5A is a cross-sectional view of the balloon dilation catheter taken along the line A-A' of FIG. 2B.
Figure 5B:
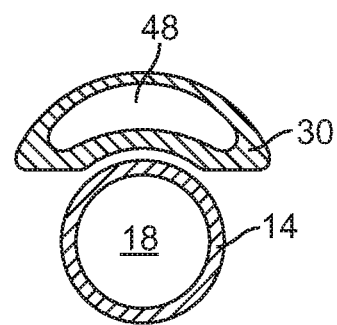
FIG. 5B is a cross-sectional view of the balloon dilation catheter taken along the line B-B' of FIG. 4.

The helical portion 52 of the shaft 30 may be formed by "skiving" away a portion of the shaft 30. FIG. 5A illustrates a cross-sectional view of the shaft 30, inner support guide 14, and support member 40 along the line A-A' of FIG. 2B. As seen in FIG. 2B, this area is distal to where the helical portion 52 of the shaft 30 is located. Referring now to FIG. 5A, the shaft 30 includes a rider lumen 54 that is dimensioned to have a diameter that is slightly larger than the outer diameter of the inner support guide 14. The rider lumen 54 thus enables the shaft 30 to advance and retract over the inner support guide 14 in a close-fit arrangement. The outer diameter of the shaft 30 may generally fall within the range of about 0.050 inch to about 0.110 inch or within the range of about 0.070 inch to about 0.100 inch. One or both of the exterior surface of the inner guide member 14 and the interior surface of the rider lumen 54 may be optionally coated with a lubricious coating to reduce frictional contact forces. FIG. 5B illustrates a cross-sectional view of the inner support guide 14 and the helical portion 52 of the shaft 30 taken along the line B-B' of FIG. 4. As seen in FIG. 5B, a portion of the shaft 30 that includes the rider lumen 54 is skived away. The result is that a single lumen (inflation lumen 48) remains in the shaft 30 that is helically wrapped about the inner support guide 14.

FIGS. 6A-6C illustrate various embodiments of an inner guide member 14. The inner guide member 14 may have a variety of shapes and configurations depending on the particular application or patient. The different shapes of the inner guide member 14 may be factory-formed in a particular shape and offered as a different model as fully assembled or, alternatively, the inner guide member 14 may be replaceable or modular elements that could slide inside the rider lumen 54 and inserted into the port 22 in a press-fit type sealing arrangement. In yet another alternative, the shapes could represent desirable shapes that a malleable inner guide member 14 could be formed into by the user to better fit a particular application or subject's anatomy.

FIG. 6A illustrates an inner guide member 14 that includes a curved distal portion 16 that terminates in a straight segment 46. In the embodiment of FIG. 6A, the curve in the curved distal portion 16 is pronounced and turns back on itself in the shape of a "U" in which the distal end 20 turns back in retrograde fashion. This embodiment may be useful to treat hard to reach ostia or other structures, e.g., the maxillary ostium or the infundibulum via a transnasal route, if the nasal anatomy will allow for a transnasal approach. While FIG. 6A illustrates a "U" shaped curve, other degrees of curvature are contemplated. FIG. 6B illustrates an inner guide member 14 according to another embodiment. In this embodiment, the curved distal portion 16 also terminates in a straight segment 46 although the radius of curvature is less pronounced. In this embodiment, the straight segment 46 may have a length within the range of about 8 mm to about 10 mm although other lengths may be used. It is believed that this embodiment is particularly suited for most frontal recess anatomy. FIG. 6C illustrates an embodiment in which the inner guide member 14 is substantially straight. This later embodiment may be particularly suited for treating the sphenoids of the subject, or straightforward frontal recess anatomy.

Figure 7:
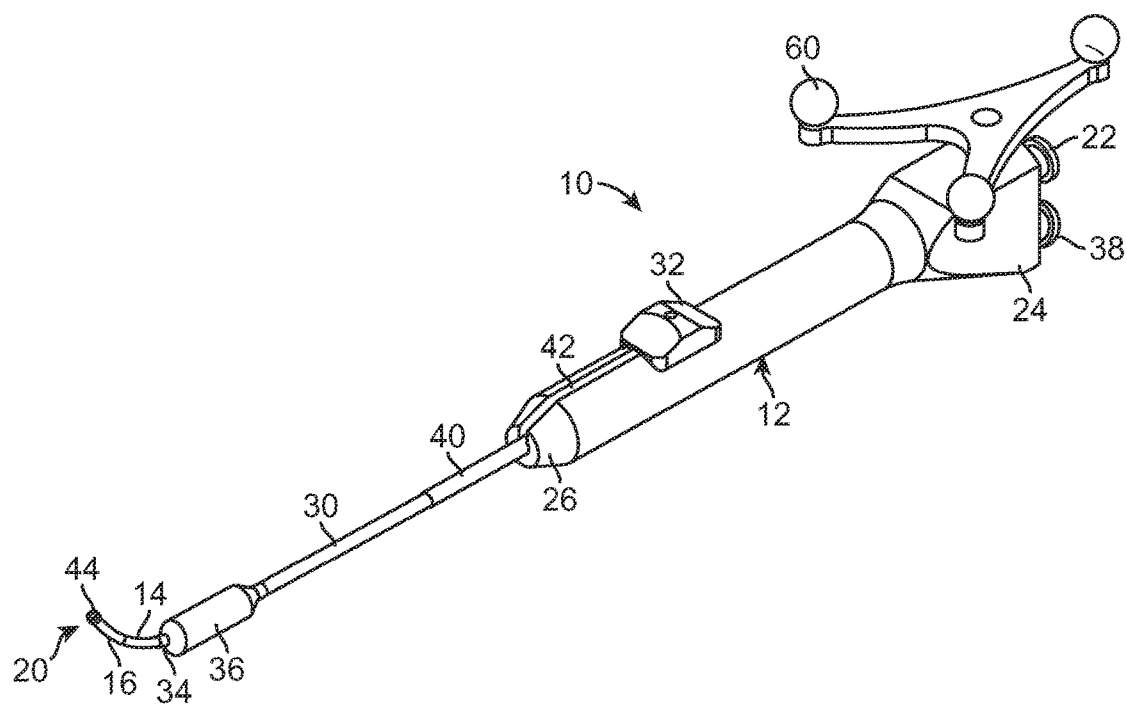
FIG. 7 illustrates a perspective view of a balloon dilation catheter according to another embodiment.

FIG. 7 illustrates a balloon dilation catheter 10 according to another embodiment. In this embodiment, a tracking element 60 is located on the handle 12 of the balloon dilation catheter 10. The tracking element 60 may include an antenna, transmitter, optical reflectors, or the like that communicates a wireless signal that is then received and processed to determine the orientation and/or positioning of the balloon dilation catheter 10. In certain embodiments, more than one tracking element 60 may be disposed on the balloon dilation catheter 10. Data regarding the orientation and/or positioning of the balloon dilation catheter 10 may then be processed and displayed on the display for viewing by the physician. For example, image guided surgery is becoming increasingly commonplace, permitting physicians to review real time actual or virtual images of a particular device within a subject during a surgical procedure.

For example, U.S. Pat. Nos. 5,391,199 and 5,443,489, which are incorporated by reference, describe a system wherein coordinates of an intrabody probe are determined using one or more field sensors such as, Hall effect devices, coils, or antennas that are carried on the probe. U.S. Patent Application Publication No. 2002-0065455, which is also incorporated by reference, describes a system that is capable of generating a six-dimensional position and orientation representation of the tip of a catheter using a combination of sensor and radiation coils. U.S. Patent Application Publication No. 2008-0269596, which is also incorporated by reference, describes yet another monitoring system that has particular applications in orthopedic procedures. Commercial systems such as the LANDMARX Element (Medtronic Xomed Products, Inc., Jacksonville, Fla.) are available for use in conjunction with ENT procedures.

In the embodiment of FIG. 7, the tracking element 60 permits accurate tracking of the distal end 20 of the balloon dilation catheter 10 such that an image of distal portion of the balloon dilation catheter 10 may be superimposed on a patient's anatomical imagery. For example, a previously conducted computed tomography (CT) scan of the patient may be used to generate a visual image of the patient's anatomical regions of interest. Based on the location of the tracking element 60, an image guided surgery (IGS) system can then superimpose an image of the balloon dilation catheter 10 onto the image to better enable the physician to manipulate and orient the balloon dilation catheter 10.

Other commercial systems may also be used in connection with the balloon dilation catheter 10 illustrated in FIG. 7. For example, the INSTATRAK 3500 Plus—ENT from GE Healthcare, Chalfont St. Giles, United Kingdom may be integrated and/or used with the balloon dilation catheter 10. The use of CT guidance to position the balloon dilation catheter 10 is preferred because the device may be positioned by the operator with just a single hand, while viewing the CT image interface (e.g., display) at the same time the handle 12 is manipulated. Optionally, the balloon dilation catheter 10 may be initially positioned using and endoscope or other visualization tool. For instance, a conventional "Hopkins rod" endoscope (not shown) may be manipulated alongside the balloon dilation catheter 10 to aid in placement.

Figure 8:
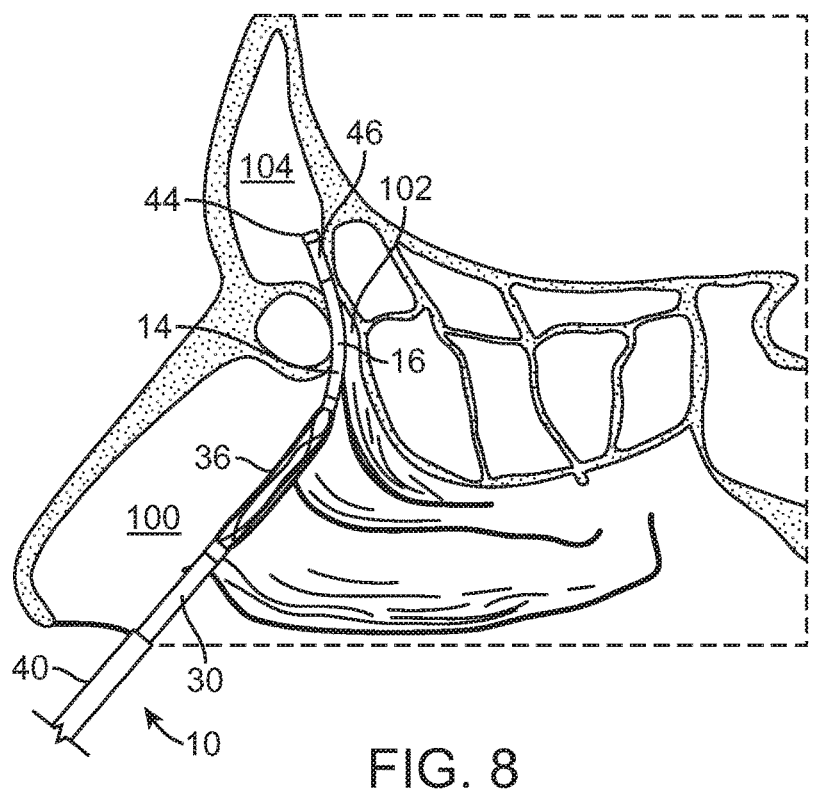
FIG. 8 illustrates a cross-sectional view of the frontal sinus of a subject with the inner guide member of the balloon dilation catheter being advanced into the subject's frontal recess.

FIGS. 8-12 illustrate various cross-sectional views (sagittal plane) of the frontal sinus of a subject undergoing treatment with a balloon dilation catheter 10. The cross-sectional views illustrate the nasal passageway 100, the frontal recess 102, and the frontal sinus cavity 104. Referring to FIG. 8, the balloon dilation catheter 10 is inserted into the nasal passageway 100 with the advancer knob 32 in the retracted position (e.g., as illustrated in FIG. 1, 2A, 2B) such that the shaft 30 and balloon 36 are also retracted proximally. In addition, the balloon 36 is in a deflated state as seen in FIG. 8. The curved portion 16 of the inner guide member 14 is then positioned within the frontal recess 102 of the subject as seen in FIG. 8. This positioning of the inner guide member 14 may be accomplished under endoscopic visualization using a conventional endoscope such as a Hopkins rod-type endoscope that is positioned alongside the balloon dilation catheter 10. Alternatively, the inner guide member 14 may be positioned using IGS techniques that track the position of the balloon dilation catheter 10 using one or more tracking elements 60 as illustrated, for instance, in the embodiment of FIG. 7. For instance, the inner guide member 14 may be advanced under guidance from CT imaging.

Figure 9:
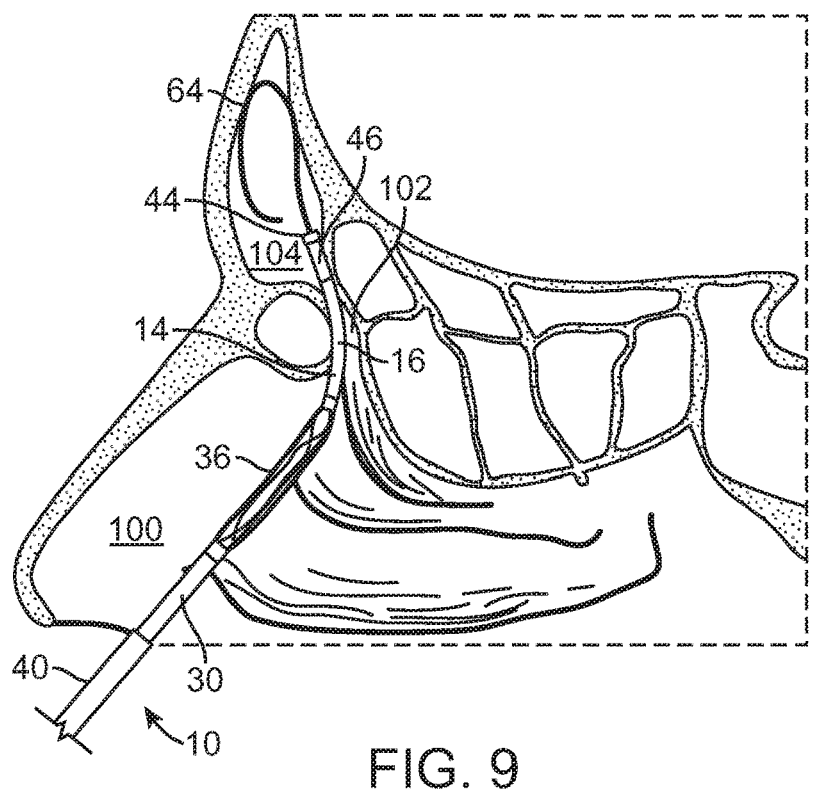
FIG. 9 illustrates a cross-sectional view of the frontal sinus of a subject with the inner guide member of the balloon dilation catheter being positioned in the subject's frontal recess. A guide wire is shown advanced through the catheter and into the subject's frontal sinus cavity.

Referring now to FIG. 9, confirmation of accurate positioning of the inner guide member 14 within the frontal recess 102 may be accomplished by placement of a fluoroscopically visible guide wire 64 through the lumen 18 of the inner guide member 14. The guide wire 64 may be inserted into the lumen 18 via the port 22. Under fluoroscopic visualization, the guide wire 64 can be seen to advance into the frontal sinus cavity 104 once the inner guide member 14 is positioned properly within the frontal recess 102. If the guide wire 64 does not advance into the frontal sinus cavity 104, the balloon dilation catheter 10 is re-positioned and confirmation is subsequently attempted. As an alternative to a fluoroscopically visible guide wire 64, the guide wire 64 could be a light emitting guide wire such as that disclosed in U.S. Patent Application Publication No. 2007-0249896, which is incorporated by reference herein. Of course, the guide wire 64 is optional as the inner guide member 14 may be placed without the aid or need for the same. Alternatively, the guide wire 64 could be positioned in the frontal sinus initially, prior to placement of the balloon catheter 10.

Figure 10:
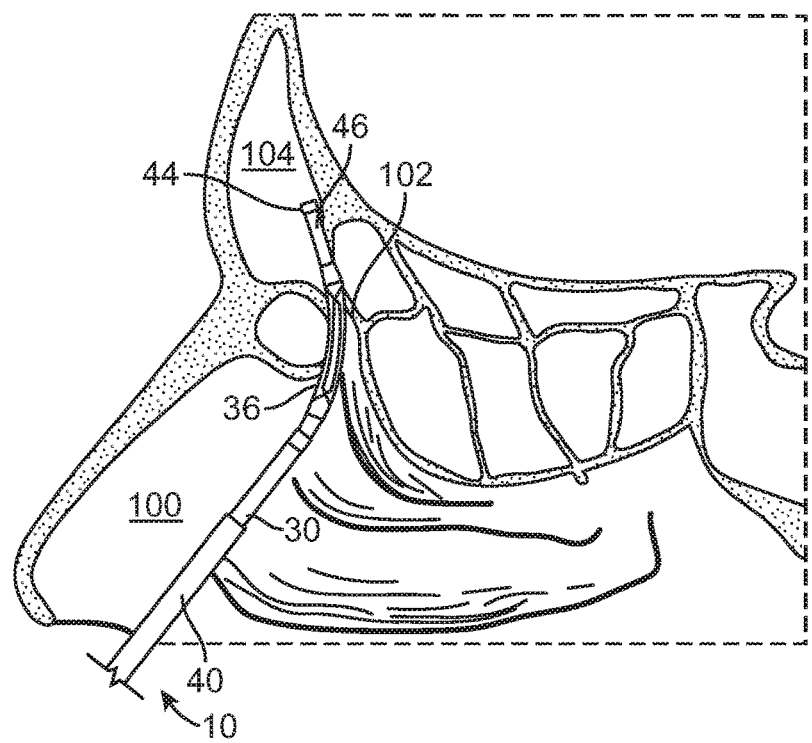
FIG. 10 illustrates a cross-sectional view of the frontal sinus of a subject with the balloon (in a deflated state) and shaft being advanced into the subject's frontal recess.
Figure 11:
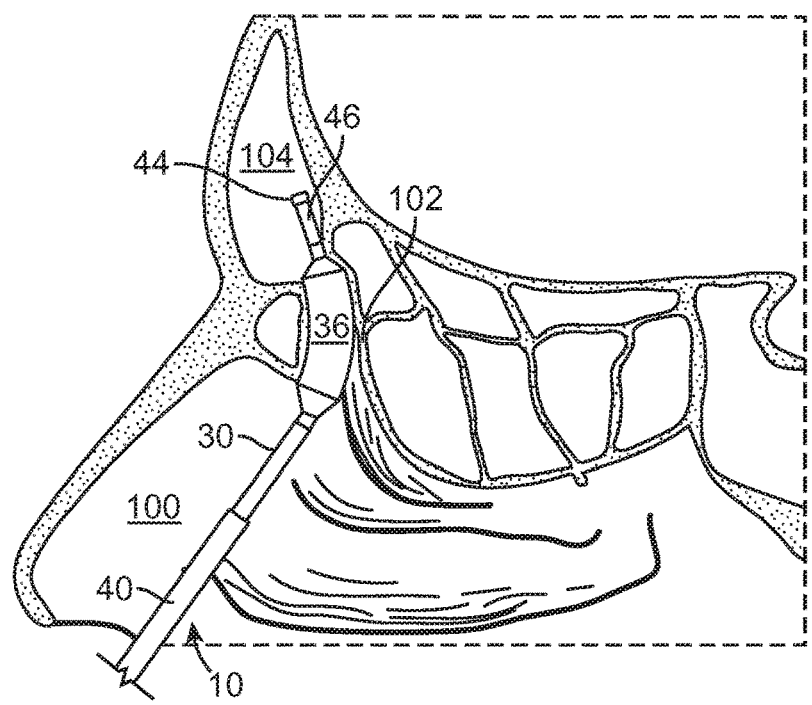
FIG. 11 illustrates a cross-sectional view of the frontal sinus of a subject with the balloon of FIG. 10 in an inflated state to thereby widen and remodel the frontal recess.

Now referring to FIG. 10, once the curved portion 16 of the inner guide member 14 is properly positioned, the advancer knob 32 is advanced in the distal direction (arrow A of FIG. 3A) thereby advancing the shaft 30 and attached balloon 36 into the frontal recess 102. This is illustrated in FIG. 10. After the balloon 36 is positioned in the frontal recess 102, the balloon 36 is inflated as illustrated in FIG. 11. Inflation is accomplished by coupling an inflation device (not shown) to the port 38. The inflation device may include a syringe or the like that is depressed to infuse a fluid into the inflation lumen 48 which then passes into the interior of the balloon 36 to effectuate expansion of the balloon 36 to the state illustrated in FIG. 11. Pressures typically used to accomplish widening or remodeling of the frontal recess 102 are within the range of about 3 atmospheres to about 12 atmospheres. The balloon 36 may be inflated only a single time or, alternatively, the balloon 36 may be inflated, deflated, and inflated again a plurality of times in order to achieve the desired degree of widening. Each inflation step may be performed after positioning the balloon 36 in a different position within the frontal recess 102.

Figure 12:
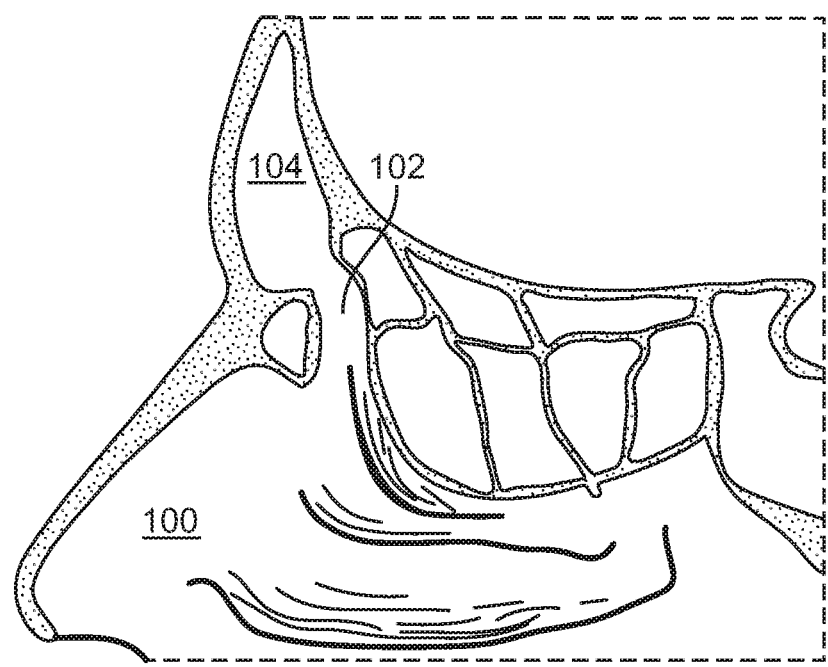
FIG. 12 illustrates a cross-sectional view of the frontal sinus of a subject after the frontal sinus has been widened and the balloon inflation catheter withdrawn.

After the frontal recess 102 has been widened or otherwise remodeled, the balloon 36 is deflated and removed as illustrated in FIG. 12. The widened frontal recess 102 illustrated in FIG. 12 is believed to restore the drainage and aeration function and health of the frontal sinus cavity 104. Deflation of the balloon 36 is accomplished by reducing the fluid pressure within the interior of the balloon 36. For example, the plunger of a syringe or the like that is fluidically coupled to the port 38 may be withdrawn to remove fluid from the interior of the balloon 36. The balloon dilation catheter 10 can then be withdrawn proximally from the nasal passageway 100.

In certain patients, treatment of one or both frontal sinuses 104 as described above may be adequate. In other patients, additional sinuses may need to be treated, particularly the maxillary and/or anterior ethmoid sinuses. In such patients, a combination procedure may be well suited. The maxillary and/or anterior ethmoid sinuses can be treated with a system such as described in U.S. Pat. No. 7,520,876 and U.S. Patent Application Publication No. 2008-0172033, commercially available as the FinESS system by Entellus Medical, Inc. of Maple Grove, Minn. Alternatively, other sinuses could be treated more conventionally using surgical techniques such as, for instance, functional endoscopic sinus surgery (FESS).

Also, the sphenoid and/or maxillary sinus outflow tracts could be dilated with the embodiment of the balloon catheter 10 described above. It is also contemplated that the balloon catheter 10, particularly the embodiment of FIG. 7 with a suitable IGS device is incorporated, and with an appropriate shape for the inner support member 14, preferably straight as illustrated in FIG. 6C, could be used to dilate the maxillary sinus outflow tract via the canine fossa route. Suitable access tools are described in co-pending U.S. Patent Application Publication No. 2009-0216196, which is incorporated by reference herein. This could be performed without need for additional endoscopic visualization, permitting treatment through a relatively small diameter access passageway into the sinus cavity in the region of the canine fossa. A small endoscope (not shown) could be utilized, if desired, through the lumen 18 of the inner support member 14 to further aid in visualization of the maxillary sinus outflow tract.

While embodiments of the present invention have been shown and described, various modifications may be made without departing from the scope of the present invention. The invention, therefore, should not be limited, except to the following claims, and their equivalents.

What is claimed is:

1. A balloon dilation catheter for dilating sinus drainage pathways, the balloon dilation catheter comprising:
   a handle having a proximal end and a distal end and a slot disposed in a surface of the handle, the handle configured to be gripped by an operator;
   a substantially rigid inner guide member having a blunt distal end and a proximal end and a lumen extending between the distal end and the proximal end, the substantially rigid inner guide member extending longitudinally from the distal end of the handle and wherein the proximal end of the substantially rigid inner guide member terminates within the handle;
   a shaft slidably arranged over the substantially rigid inner guide member, the shaft including an inflation lumen that is fluidically coupled to an inflation port, and wherein a distal portion of the shaft includes an inflatable balloon;
   a shaft advancing member that is moveable along the slot disposed in the surface of the handle, wherein moving the shaft advancing member along the slot moves the shaft over the substantially rigid inner guide member; and
   a flexible guide wire disposed within the lumen of the substantially rigid inner guide member.

2. The balloon dilation catheter of claim 1, wherein the substantially rigid inner guide member comprises a metallic hypotube.

3. The balloon dilation catheter of claim 1, wherein the flexible guide wire is a light emitting guide wire.

4. The balloon dilation catheter of claim 1, wherein the shaft defines a rider lumen coated with a lubricious coating and the substantially rigid inner guide member extends through the rider lumen.

5. The balloon dilation catheter of claim 1, wherein a distal portion of the substantially rigid inner guide member is curved and defines a radius of curvature between about 0.25 inches and about 1.5 inches.

6. The balloon dilation catheter of claim 1, wherein the shaft advancing member is coupled directly to the shaft.

7. The balloon dilation catheter of claim 1, wherein the flexible guide wire extends through the handle and beyond a distal end of the substantially rigid inner guide member.

8. A balloon dilation catheter for dilating sinus drainage pathways, the balloon dilation catheter comprising:
   a handle configured to be gripped by an operator, the handle including a proximal end, a distal end, and a side surface extending between the proximal end and the distal end, wherein a slot extends along a length of the side surface;

a substantially rigid inner guide member extending longitudinally from the distal end of the handle and terminating at one end in a blunt distal tip and terminating at an opposing, proximal end that is located within the handle, the substantially rigid inner guide member having a lumen extending along a length thereof between the proximal end and the distal tip;

a flexible guide wire disposed within the lumen of the substantially rigid inner guide member;

a shaft slidably arranged over the substantially rigid inner guide member, wherein a distal portion of the shaft includes an inflatable balloon; and a shaft advancing member that is moveable along the slot, wherein moving the shaft advancing member along the slot slides the shaft over the substantially rigid inner guide member.

9. The balloon dilation catheter of claim 8, wherein the substantially rigid inner guide member comprises a stainless steel hypotube.

10. The balloon dilation catheter of claim 8, wherein the flexible guide wire is a light emitting guide wire.

11. The balloon dilation catheter of claim 8, wherein the shaft defines a rider lumen coated with a lubricious coating and the substantially rigid inner guide member extends through the rider lumen.

12. The balloon dilation catheter of claim 8, wherein a distal portion of the substantially rigid inner guide member is curved and defines a radius of curvature between about 0.25 inches and about 1.5 inches.

13. The balloon dilation catheter of claim 8, wherein the shaft advancing member is coupled to the shaft.

14. A balloon dilation catheter for dilating sinus drainage pathways, the balloon dilation catheter comprising:

a handle having a proximal end and a distal end and a slot disposed in a surface of the handle, the handle configured to be gripped by an operator;

a substantially rigid inner guide member extending longitudinally from the handle in a distal direction, wherein the substantially rigid inner guide member comprises a hypotube having a proximal end that terminates within the handle and a blunt distal tip, the hypotube defining a lumen that extends from the proximal end to the blunt distal tip, wherein a flexible guide wire is arranged within the lumen;

a shaft slidably arranged over the substantially rigid inner guide member, wherein a distal portion of the shaft includes an inflatable balloon, wherein the shaft defines a rider lumen; and a shaft advancing member that is coupled to the shaft and moveable along the slot disposed in a surface of the handle, wherein moving the shaft advancing member along the slot moves the shaft over the substantially rigid inner guide member and the rider lumen and/or shaft are coated with a lubricious coating.

15. A balloon dilation catheter for dilating sinus drainage pathways, the balloon dilation catheter comprising:

a handle configured to be gripped by an operator, the handle including a proximal end, a distal end, and a side surface extending between the proximal end and the distal end, wherein a slot extends along a length of the side surface;

a substantially rigid inner guide member extending in a distal direction from the distal end of the handle, the substantially rigid inner guide member comprising a proximal end that terminates within the handle and a blunted distal tip that is configured to not penetrate tissue;

a shaft slidably arranged over the substantially rigid inner guide member, wherein a distal portion of the shaft includes an inflatable balloon and an inflation lumen that is in fluid communication with an interior of the inflatable balloon;

a shaft advancing member that is coupled to the shaft and moveable along the slot, wherein moving the shaft advancing member along the slot slides the shaft over the substantially rigid inner guide member, wherein the substantially rigid inner guide member defines a lumen and a flexible guide wire is arranged within the lumen; and a support member extending along a length of the shaft and surrounding the substantially rigid inner guide member.

16. The balloon dilation catheter of claim 15, wherein the support member comprises a metallic tube.

* * * * *